United States Patent [19]

Pechhold

[11] 4,383,100

[45] May 10, 1983

[54] POLYURETHANES FROM OLIGOMERIC FORMAL DIOLS OF THF COPOLYMER GLYCOLS

[75] Inventor: Engelbert Pechhold, Chadds Ford, Pa.

[73] Assignee: E. I. Du Pont de Nemours and Company, Wilmington, Del.

[21] Appl. No.: 340,828

[22] Filed: Jan. 19, 1982

Related U.S. Application Data

[62] Division of Ser. No. 188,877, Sep. 19, 1980, Pat. No. 4,273,693.

[51] Int. Cl.$^3$ .................... C08G 18/48; C07C 42/30
[52] U.S. Cl. ..................................... 528/76; 521/158; 528/249; 568/601
[58] Field of Search .................. 521/158; 528/76, 230, 528/249; 568/601

[56] References Cited

U.S. PATENT DOCUMENTS

| | | | |
|---|---|---|---|
| 2,961,428 | 11/1960 | Muller et al. | 260/49 |
| 3,425,999 | 2/1969 | Axelwood et al. | 528/76 |
| 3,959,227 | 5/1976 | Chang et al. | 260/67 |
| 4,090,990 | 5/1978 | Singh et al. | 528/76 |

FOREIGN PATENT DOCUMENTS 850178  9/1960  United Kingdom .

OTHER PUBLICATIONS

Schonfeld, Journal of Polymer Science, vol. 59, pp. 87–92 (1962).

*Primary Examiner*—H. S. Cockeram

[57] ABSTRACT

Oligomeric formal diols are prepared by coupling segments of copolyether glycols with formaldehyde. The formal diols are useful in preparing polyurethanes.

6 Claims, No Drawings

POLYURETHANES FROM OLIGOMERIC FORMAL DIOLS OF THF COPOLYMER GLYCOLS

CROSS-REFERENCE TO RELATED APPLICATION

This application is a divisional of copending application Ser. No. 188,877, filed Sept. 19, 1980, now U.S. Pat. No. 4,273,693.

DESCRIPTION

Technical Field

This invention relates to oligomeric formal diols of copolyether glycols. It is more particularly directed to such formal diols made by coupling copolyether glycol segments with formaldehyde.

The invention also relates to polyurethanes made with these oligomeric formal diols.

Background and Summary of the Invention

Polyurethanes have been known and used for many years, and the basic general chemistry for their preparation, the reaction of a polyol, a polyisocyanate and a chain extender, is well documented.

A type of polyol sometimes used for this purpose is the copolyether glycol based on tetrahydrofuran (THF) and an alkylene oxide (AO). In some applications, especially where a polyurethane of high modulus and hardness is needed, it is desirable to use a copolyether glycol with a molecular weight of over about 2000. Unfortunately, a copolyether glycol of such high molecular weight is difficult to make and use because its high viscosity hinders handling and subsequent reaction.

It has now been found that this difficulty can be eliminated by using a product made by coupling segments of the copolyether glycol with formaldehyde. This gives an oligomeric formal diol with a viscosity much lower than that of the conventional copolyether glycol of equivalent molecular weight. Moreover, when such a formal diol is used to prepare a polyurethane, the product shows no significant degradation of properties when compared to one made with a conventional copolyether glycol of equivalent molecular weight.

DETAILED DESCRIPTION OF THE INVENTION

The oligomeric formal diols of the invention are made by catalytically reacting a suitable copolyether glycol with formaldehyde.

The copolyether glycol starting material is one based on THF and an AO, and is sometimes also referred to as a copolymer of THF and an AO. "AO" as used herein, means an alkylene oxide whose ring contains two or three carbon atoms. The AO can be unsubstituted or substituted with, for example, alkyl groups or halogen atoms. Illustrative alkylene oxides are ethylene oxide (EO), 1,2-propylene oxide (PO), 1,3-propylene oxide, 1,2-butylene oxide, 1,3-butylene oxide, 2,2'-bis-chloromethyl-1,3-propylene oxide and epichlorohydrin. The copolymers preferred for use are those of THF and EO and THF and PO. The copolymer can also be of THF and two or more alkylene oxides, as for example a THF/EO/PO polymer.

The copolymer will have (1) 10–80%, by weight, of AO units, preferably 20–60%, even more preferably 30–55%; and (2) hydroxyl functionalities of 2.0–4.0, preferably 2.0–2.5.

The copolyether glycol starting material can be of any practical molecular weight, but will preferably have a number average molecular weight of 600–4000, even more preferably 1000–3000. Number average molecular weight is determined by first determining the hydroxyl number of the sample by titrating it with acetic anhydride according to ASTM-D-1638 and then converting this number to number average molecular weight according to the formula $$\text{Molecular weight} = \frac{56{,}000 \times n}{\text{hydroxyl number}}$$

where n is the hydroxyl functionality of the sample.

The copolyether glycol can be produced by any of the known methods. Illustrative of such methods are those shown in British Pat. No. 854,958 and U.S. Pat. No. 4,127,513. The disclosures of those documents are incorporated into this application to show how such copolymers are prepared.

The formaldehyde can be used as a gas, as an aqueous solution, or in the form of paraformaldehyde. As used herein, "formaldehyde" means any of these forms. If an aqueous solution is used, the water thus introduced must later be removed from the reaction mass, and the use of paraformaldehyde is therefore preferred.

The amounts of copolyether glycol and formaldehyde used are of course governed by the molecular weight desired in the product and concomitantly, the number of glycol segments that are to be coupled. It is preferred to use an excess of paraformaldehyde when it is used because it has a tendency to sublime under reaction conditions; it is desirable that this loss be compensated for.

The coupling reaction can be carried out in an aromatic hydrocarbon like toluene or xylene, or it can be carried out in bulk, using the copolyether glycol itself as the reaction medium.

The catalyst can be any strongly acidic cationic ion-exchange resin bearing —SO$_3$H groups, insoluble in the copolyether glycol. "Insoluble" means that the amount of resin which dissolves in the glycol under process conditions will give the formal diol product an acid number of no greater than 0.05 mg of KOH per gram.

For purposes of the invention, the nature of the "backbone" of the ion-exchange resin is unimportant. The most common of the commercially available resins of this type have backbones which are of the polystyrene type, but resins having other backbones can be used. Preferred among the polystyrene-type resins, and preferred for use, is one sold by the Rohm & Haas Company of Philadelphia, PA, as Amberlyst® XN-1010. This macroreticular resin has a cation exchange capacity of 3.1 milliequivalents per gram, a surface area of 450 square meters per gram, a porosity of 41%, and a mean pore diameter of 50 Angstrom units.

The catalyst is used at a concentration of 1–10%, by weight of the copolyether glycol, preferably 5–10%.

The reaction is carried out at a temperature of 60°–110° C., preferably 70°–90° C. If the reaction is conducted in an aromatic hydrocarbon medium, the water of condensation formed can be removed by azeotropic distillation. If it is conducted in bulk, the water can be removed under vacuum or by sweeping the reaction zone with nitrogen.

When an oligomeric formal diol having the desired molecular weight has been obtained, as determined by periodic sampling and analysis, the reaction mass is cooled to ambient temperature and the catalyst and unreacted paraformaldehyde (if it is used) are removed by filtration. If formaldehyde is used, any which remains unreacted can be removed under vacuum.

Any number of copolyether ether segments can be coupled in this manner. The simplest oligomeric formal diol is of course that formed by coupling two glycol segments. The upper limit of the number of segments which can be coupled is a practical one: beyond a certain range, the viscosity of the product makes preparation self-limiting. Most commercial and industrial applications will require a formal diol with a number average molecular weight in the range 1200–12,000, more preferably 4000–9000.

The formal diol will be a liquid at room temperature and will have a viscosity within the range 0.5–10.0 pascal seconds, as determined at 60° C. with a glass capillary viscometer, according to ASTM-D-445 and ASTM-D-2515.

A polyurethane can be prepared from such an oligomeric formal diol by reacting it with an organic polyisocyanate and an aliphatic polyol or polyamine chain extender, as is well known in the art.

The polyisocyanates used in preparing the polyurethanes can be any of the aliphatic or aromatic polyisocyanates ordinarily used to prepare polyurethanes. Illustrative are
2,4-toluene diisocyanate
2,6-toluene diisocyanate
hexamethylene-1,6-diisocyanate
tetramethylene-1,4-diisocyanate
cyclohexane-1,4-diisocyanate
naphthalene-1,5-diisocyanate
diphenylmethane-4,4'-diisocyanate
xylylene diisocyanate
hexahydro xylylene diisocyanate
dicyclohexylmethane-4,4'-diisocyanate
1,4-benzene diisocyanate
3,3'-dimethoxy-4,4'-diphenyl diisocyanate
m-phenylene diisocyanate
isophorone diisocyanate
polymethylene polyphenyl isocyanate
4,4'-biphenylene diisocyanate
4-isocyanatocyclohexyl-4'-isocyanatophenyl methane
p-isocyanatomethyl phenyl isocyanate.
Mixtures of isocyanates can also be used.

The isocyanates preferred for use because of the desirable properties they confer on the polyurethane products are diphenylmethane-4,4'-diisocyanate and the toluene diisocyanates.

The chain extenders used in preparing the polyurethanes can be any of the aliphatic polyols or any of the aliphatic or aromatic polyamines ordinarily used to prepare polyurethanes.

Illustrative of the aliphatic polyols which can be used as chain extenders are
1,4-butanediol
ethylene glycol
1,6-hexanediol
glycerine
trimethylolpropane
pentaerythritol
1,4-cyclohexane dimethanol
phenyl diethanolamine.

Diols like hydroquinone bis(betahydroxyethyl)ether, tetrachlorohydroquinone-1,4-bis(betahydroxyethyl)ether and tetrachlorohydroquinone-1,4-bis(betahydroxyethyl) sulfide, even though they contain aromatic rings, are considered to be aliphatic polyols for purposes of the invention.

Aliphatic diols of 2–10 carbon atoms are preferred. Especially preferred is 1,4-butanediol. Mixtures of diols can also be used.

Illustrative of the polyamines which can be used as chain extenders are
p,p'-methylene dianiline and complexes thereof with alkali metal chlorides, bromides, iodides, nitrites and nitrates.
4,4'-methylene bis(2-chloroaniline)
dichlorobenzidine
piperazine
2-methylpiperazine
oxydianiline
hydrazine
ethylenediamine
hexamethylenediamine
xylylenediamine
bis(p-aminocyclohexyl)methane
dimethyl ester of 4,4'-methylenedianthranilic acid
p-phenylenediamine
m-phenylenediamine
4,4'-methylene bis(2-methoxyaniline)
4,4'-methylene bis(N-methylaniline)
2,4-toluenediamine
2,6-toluenediamine
benzidine
3,4'-dimethylbenzidine
3,3'-dimethoxybenzidine
dianisidine
1,3-propanediol bis(p-aminobenzoate)
isophorone diamine
1,2-bis(2'-aminophenylthio)ethane.

The amines preferred for use are 4,4'-methylene bis(2-chloroaniline), 1,3-propanediol bis(p-aminobenzoate), and p,p'-methylenedianiline and complexes thereof with alkali metal chlorides, bromides, iodides, nitrites and nitrates. Mixtures of amines can also be used.

The polyurethanes can be prepared in two steps, the first of which is conducted under nitrogen at ambient pressure to prevent oxidation of the reactants and product, and to prevent exposure of the reaction mass to atmospheric moisture. In the first step, the oligomeric formal diol starting material is dried by heating it at a temperature of 80°–100° C. under vacuum, and is then held at 60°–125° C., preferably about 70°–90° C., while a stoichiometric excess, preferably twofold to tenfold, of organic diisocyanate is added, with stirring. The actual amount of isocyanate used depends on the molecular weight of the oligomeric formal diol, as is well known in the art. The reaction mass is held for about 1–4 hours at 60°–125° C., with stirring, and the free isocyanate content of the mass is then determined by titrating it with di-n-butylamine, as described in Analytic Chemistry of the Polyurethanes, Volume XVI, Part III, D. J. David and H. B. Staley, Wiley-Interscience, 1969, pages 357–359.

In the second step, an amount of polyamine or polyol chain extender calculated to give an isocyanate/hydroxyl or amine mole ratio of about 0.9–1.1/1 in the reaction mass, preferably 1–1.05/1, is degassed at about 30°–120° C. and 1330–5330 Pa (10–50 mm Hg) pressure and quickly added to the reaction mass.

A conventional curing catalyst can be added at this point if desired. Illustrative of catalysts which can be used are dibutyltin dilaurate and stannous octoate. The catalyst can be added to the reaction mass to give a concentration of about 0.001–0.1%, by weight, preferably about 0.01%.

The reaction mass is held with stirring at 60°–130° C. until it is homogeneous, which normally takes 1–5 minutes. The mass is then poured into molds, preferably preheated to 100°–120° C., and then cured at about 100°–120° C. at a pressure of 1700–2500 kPa for from 5 minutes to several hours. The casting is then cooled, removed from the mold, aged for about one week at ambient temperature, and is then ready for use.

The polyurethanes can also be made by reaction-injection and liquid-injection molding techniques, whereby the starting materials are simultaneously injected and mixed in a mold, preferably together with a conventional polyurethane catalyst, and then subjected to pressures ranging from ambient to several million pascals and temperatures ranging from ambient to 150° C. Use of a foaming agent such as a fluorocarbon or water is optional.

The polyurethanes thus prepared are characterized by their high modulus and hardness, which suits them for use in fabricating automobile bumpers, cast tires and the like.

BEST MODE

In the following description, all parts are by weight.

| A reactor was charged with | |
|---|---|
| THF/EO copolymer (63/37) | 550 parts |
| $M_n$ 1029 | (0.53 mol) |
| Paraformaldehyde | 35.2 parts |
| | (1.17 mols) |
| Amberlyst ® XN-1010 | 27.5 parts |

This mixture was heated to and held at 100° C. and a pressure of 5330 Pa for four hours, with stirring, while volatiles, mainly water and THF, were continuously withdrawn.

The mixture was then cooled to about 60° C., the vacuum released and the catalyst resin removed by filtration, to give a clear oligomeric formal diol with a number average molecular weight of 3336 and a viscosity of 1.11 pascal seconds at 60° C.

131 Parts of the diol were dried for one hour at 85° C. under a vacuum of 1333–5330 Pa. The diol was then cooled to 60°–70° C. and to it were then added, with stirring, 52.9 parts of diphenylmethane-4,4'-diisocyanate. A nitrogen sweep of the reaction zone was begun. Stirring was continued for 5 minutes, and the mixture was then again brought to and held at 85° C., with stirring, for 2 hours, to give a product having a free isocyanate content of 7.73%, as determined by the di-n-butylamine titration technique.

176.2 Parts of the resulting prepolymer were then heated at 85° C. for one hour under a vacuum of 1333–5330 Pa to remove entrapped air. Heating was then stopped and to the mixture were added, with stirring, 13.9 parts of 1,4-butanediol, preheated to 60° C. This mixture was stirred for 5 minutes and then poured into molds preheated to 110° C., which were then pressed in a platen press at 110° C. and a platen pressure of 2155 kPa for 17 hours. The resulting elastomeric material was held for one week at ambient temperature and was then ready for use.

I claim:

1. A polyurethane which is the reaction product of
   (a) an oligomeric formal diol made by coupling segments of copolymers of tetrahydrofuran and an alkylene oxide whose ring contains 2 or 3 carbon atoms with formaldehyde, the diol having a number average molecular weight of 1200–12000,
   (b) an organic polyisocyanate, and
   (c) a chain extender.
2. The polyurethane of claim 1 in which the polyisocyanate is diphenylmethane-4,4'-diisocyanate or a toluene diisocyanate.
3. The polyurethane of claim 1 in which the chain extender is an aliphatic polyamine or an aromatic polyamine.
4. The polyurethane of claim 3 in which the chain extender is an aliphatic diol of 2–10 carbon atoms.
5. The polyurethane of claim 4 wherein the aliphatic diol is 1,4-butanediol.
6. An oligomeric formal diol made by coupling copolyether glycol segments with formaldehyde.

* * * * *